United States Patent
Detrick et al.

(10) Patent No.: US 9,914,679 B2
(45) Date of Patent: Mar. 13, 2018

(54) PROCESSES FOR REMOVING ENTRAINED IONIC LIQUID FROM A HYDROCARBON PHASE

(71) Applicant: UOP LLC, Des Plaines, IL (US)

(72) Inventors: Kurt Detrick, Glen Ellyn, IL (US); David A. Wegerer, Lisle, IL (US); Robert J. Schmidt, Barrington, IL (US); Trung Pham, Mount Prospect, IL (US); Avram M. Buchbinder, Chicago, IL (US); Praneeth D. Edirisinghe, Chicago, IL (US); Susie C. Martins, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 73 days.

(21) Appl. No.: 14/568,970

(22) Filed: Dec. 12, 2014

(65) Prior Publication Data

US 2016/0168058 A1     Jun. 16, 2016

(51) Int. Cl.
| | |
|---|---|
| *C07C 7/12* | (2006.01) |
| *C07C 7/13* | (2006.01) |
| *C07C 2/56* | (2006.01) |
| *C07C 2/60* | (2006.01) |
| *C07C 2/74* | (2006.01) |
| *B01J 38/48* | (2006.01) |

(Continued)

(52) U.S. Cl.
CPC .............. *C07C 7/12* (2013.01); *B01J 31/0277* (2013.01); *B01J 31/4069* (2013.01); *B01J 38/48* (2013.01); *C07C 2/74* (2013.01); *C07C 7/13* (2013.01); *B01J 2231/44* (2013.01); *B01J 2531/002* (2013.01); *B01J 2531/008* (2013.01)

(58) Field of Classification Search
CPC .... C07C 7/12; C07C 7/13; C07C 2/56; C07C 2/60
USPC ....... 585/802, 820, 823, 824, 825, 826, 718, 585/719, 727, 728
See application file for complete search history.

(56) References Cited

U.S. PATENT DOCUMENTS

| | | | |
|---|---|---|---|
| 5,888,402 A | 3/1999 | Hommeltoft et al. | |
| 6,123,836 A | 9/2000 | Hommeltoft et al. | |

(Continued)

FOREIGN PATENT DOCUMENTS

| | | |
|---|---|---|
| CN | 101899487 A | 12/2010 |
| CN | 102641727 A | 8/2012 |

(Continued)

OTHER PUBLICATIONS

The International Search Report dated Jun. 15, 2016 in International Application No. PCT/US2015/064030.

(Continued)

*Primary Examiner* — Thuan D Dang

(57) ABSTRACT

One or more processes for recovering entrained ionic liquid from a hydrocarbon phase containing droplets of ionic liquid are described. The processes includes contacting the hydrocarbon phase containing the droplets of ionic liquid with a retaining material in a separation zone. The droplets of ionic liquid are retained by the retaining material. The ionic liquid may be recovered from the retaining material with a solvent or desorbent. The retaining material may be regenerated and the ionic liquid may be reactivated. The retaining material may be used in a wash vessel to retain or remove contaminant solids within the reactor or other vessels.

5 Claims, 3 Drawing Sheets

(51) Int. Cl.
    *B01J 31/02*     (2006.01)
    *B01J 31/40*     (2006.01)

(56) References Cited

U.S. PATENT DOCUMENTS

| | | | |
|---|---|---|---|
| 7,732,364 | B2 | 6/2010 | Chang et al. |
| 2002/0098137 | A1 | 7/2002 | Hommeltoft |
| 2004/0188350 | A1 | 9/2004 | Beste et al. |
| 2010/0130800 | A1 | 5/2010 | Luo et al. |
| 2012/0325724 | A1 | 12/2012 | Driver et al. |
| 2013/0066133 | A1 | 3/2013 | Cleverdon et al. |
| 2013/0331625 | A1* | 12/2013 | Liu .................. B01J 31/0278 585/315 |

FOREIGN PATENT DOCUMENTS

| | | |
|---|---|---|
| CN | 101899487 B | 1/2013 |
| CN | 103949216 A | 7/2014 |
| DE | 102008040365 A1 | 1/2009 |
| EP | 0595755 B1 | 4/1996 |
| WO | WO 2013/002908 A2 | 1/2013 |
| WO | WO 2013/002908 A3 | 1/2013 |

OTHER PUBLICATIONS

Planovskiy A.N. et al. Protsessy i. apparaty khimicheskoy tekhnologii. M., Goskhimizdat, 1962, p. 722, 723.

Katsman et al., "Interphase Distribution of Triflic Acid and Acid-Soluble Oil in the Isobutane Alkylation with Olefins," Kinetics and Catalysis (2003), 44(6), 757-760.

Lemus et al., "On the Kinetics of Ionic Liquid Adsorption onto Activated Carbons from Aqueous Solution," Industrial & Engineering Chemistry Research (2013), 52, 2969-2976.

Lemus et al., "Developing criteria for the recovery of ionic liquids from aqueous phase . . . ," Separation and Purification Technology (2012), 97, 11-19.

Qi et al., "Adsorption of 1-Butyl-3-Methylimidazolium Chloride Ionic Liquid . . . " Environmental Science & Technology (2013), 47, 2792-2798.

Palomar et al., "Adsorption of ionic liquids from aqueous effluents by activated carbon," Carbon (2009), 47, 1846-1856.

Vijayaraghavan et al., "An Assessment on the Interaction of a Hydrophilic Ionic Liquid with Different Sorbents," Industrial Engineering Chemical Research (2009), 48, 7283-7288.

Fernandez et al., "Regeneration, recovery and removal of ionic liquids," Current Organic Chemistry (2011), 15(12), 1992-2014.

* cited by examiner

PROCESSES FOR REMOVING ENTRAINED IONIC LIQUID FROM A HYDROCARBON PHASE

FIELD OF THE INVENTION

This invention relates generally to processes for removing entrained ionic liquid catalyst particles from a hydrocarbon phase and more particularly to one or more processes which use a filter material or an adsorbent material to retain the ionic liquid catalyst particles.

BACKGROUND OF THE INVENTION

Ionic liquids are essentially salts in a liquid state, and are described in U.S. Pat. Nos. 4,764,440, 5,104,840, and 5,824,832. Ionic liquids typically melt below room temperature. Ionic liquids have been used to catalyze a variety of hydrocarbon conversion processes, such as alkylation, isomerization, disproportionation, and the like. When ionic liquids are used to catalyze hydrocarbon conversion processes, the hydrocarbon feed and the ionic liquid catalyst are typically mixed with high shear to provide intimate contact. During the mixing, small droplets of ionic liquid become suspended in the immiscible, hydrocarbon phase. Some of these small droplets of ionic liquid remain entrained in the immiscible phase after conventional liquid-liquid phase separation by gravity. Since ionic liquids have a relatively high cost associated therewith, it is important to recover this entrained ionic liquid. Additionally and alternatively, depending on the downstream processing of the hydrocarbon phase, the entrained droplets can foul or damage the downstream equipment.

One method of recovering entrained ionic liquids is described in U.S. Pat. No. 8,067,656. The process involves coalescing ionic liquid droplets onto a coalescing material. Eventually, the small droplets will coalesce into larger droplets on the surface of the coalescing material. The large droplets will remove themselves from the coalescing material by falling due to their increased weight or by being carried away in the process stream due to their increased size relative to their contact area with the coalescing material. The coalesced droplets can be recovered by settling to provide an ionic liquid layer.

While this method is presumably effective for its intended purpose, such methods require the use of a coalescing material which may be undesirable in some circumstances. For example, the coalescing material can become fouled with ionic liquid and conjunct polymer. Conjunct polymers are byproducts of the hydrocarbon reactions which use ionic liquid catalysts, and the conjunct polymers form a complex with the ionic liquid catalyst. In addition to the fouling, the use of coalescing material requires a pressure drop, and building up a pressure head expends power. By coalescing material, it is meant to encompass materials which attract ionic liquid, and which have surface properties such that the materials can be fully wetted by the ionic liquid and which do not require a change in composition of the fluid in order for the ionic liquid to be removed from the coalescing material. They can be high specific surface area materials with voids or openings of a size approaching the size of the smallest droplets of ionic liquid to be removed. Examples of coalescing materials are glass beads, metal packing, fiberglass, polymer fibers, and ceramic membrane.

Another separation process is disclosed in DE 10 2008 040 365 in which a polymerization reaction is performed with an ionic liquid catalyst and an adsorbent material is used to remove droplets of the ionic liquid catalyst from the polymerized product. While presumably effective for its intended purpose, this reference does not disclose an alkylation process in which the ionic liquid catalyst droplets are entrained in an alkylate product. Furthermore, this reference fails to address the deactivation of the ionic liquid that may occur as a result of adsorption.

Therefore, there remains a need for additional effective and efficient methods of recovering entrained ionic liquids from a hydrocarbon phase.

SUMMARY OF THE INVENTION

Various processes have been invented in which entrained ionic liquid droplets are retained by a retaining material for retaining ionic liquid catalyst droplets. By "retaining ionic liquid catalyst droplets" it is meant that the droplets require a second fluid/material in order to be removed from the retaining material. Examples of the second fluid/material include a desorbent, a solvent, or the like.

Therefore, in a first aspect of the present invention, the invention may be broadly characterized as a process for removing ionic liquid catalyst from a stream including hydrocarbons and an ionic liquid catalyst by: separating a mixture comprising hydrocarbons and ionic liquid catalyst into a hydrocarbon phase and an ionic liquid catalyst phase, the hydrocarbon phase including ionic liquid catalyst droplets; and, separating the ionic liquid catalyst droplets from the hydrocarbon phase by retaining the ionic liquid catalyst droplets on a retaining material for retaining ionic liquid catalyst droplets to provide an ionic liquid catalyst lean hydrocarbon stream.

In at least one embodiment, separating the mixture comprising hydrocarbons and ionic liquid catalyst into the hydrocarbon phase and the ionic liquid catalyst phase comprises separation by gravity.

In one or more embodiments, the process comprises fractionating the ionic liquid catalyst lean hydrocarbon stream into a recycle stream and a product stream. It is preferred that the recycle stream is an iso-butane rich stream.

In various embodiments, the retaining material for retaining ionic liquid catalyst droplets comprises a filter material.

It some embodiments, the ionic liquid catalyst is removed from the retaining material with a solvent.

In some embodiments, the retaining material comprises an adsorbent material. It is contemplated that the adsorbent material comprises an oxide, such as aluminum oxide, a salt, an ion exchange resin, activated carbon, a polymer, a natural fiber, a zeolite or other molecular sieve, or a combination thereof. It is also contemplated that the process includes desorbing ionic liquid catalyst from the adsorbent material with a desorbent. It is further contemplated that the process further includes regenerating the adsorbent material.

It various embodiments, the process also includes recovering the ionic liquid from the retaining material and reactivating the ionic liquid that has been recovered. It is contemplated that the ionic liquid is reactivated with aluminum chloride.

In a second aspect of the present invention, the invention may be broadly characterized as a process for removing ionic liquid catalyst from a portion of a stream from an ionic liquid catalyst reaction zone by: performing an alkylation reaction in a reaction zone with an ionic liquid catalyst, the reaction zone being operated under conditions to provide an alkylate rich effluent stream; passing the alkylate rich effluent stream to a first separation zone, the first separation zone configured to separate the alkylate rich effluent stream into a hydrocarbon stream and an ionic liquid catalyst stream; passing the hydrocarbon stream to a second separation zone configured to separate ionic liquid catalyst droplets from the hydrocarbon stream by retaining the ionic liquid catalyst droplets on a retaining material for retaining ionic liquid catalyst droplets to provide an ionic liquid catalyst lean hydrocarbon stream; passing the ionic liquid catalyst lean hydrocarbon stream to a fractionation zone to provide an iso-butane stream and a product stream.

In at least one embodiment, the process includes recycling a portion of the ionic liquid catalyst stream to the reaction zone. It is contemplated that a portion of the ionic liquid catalyst stream is reactivated prior to being recycled to the reaction zone In one or more embodiments, the process includes recycling the iso-butane stream to the reaction zone.

In various embodiments, the process also includes recovering the ionic liquid catalyst from the retaining material. It is contemplated that the process also includes reactivating at least a portion of the ionic liquid catalyst that has been recovered from the retaining material.

In at least one embodiment, the second separation zone comprises at least two separator vessels. It is contemplated that the at least two vessels are operated in either adsorption mode or desorption mode independent from each other.

In various embodiments, the retaining material comprises a filter material. It is contemplated that the process includes passing a solvent to the second separation zone to remove solid contaminant particles from the filter material.

In one or more embodiments, the retaining material comprises an adsorbent material. It is contemplated that the process includes desorbing the ionic liquid from the adsorbent material with a desorbent. It is also contemplated that the process includes regenerating the adsorbent material. It is further contemplated that the process includes separating ionic liquid catalyst from the desorbent and reactivating the ionic liquid separated from the desorbent.

In a third aspect of the present invention, the invention may be broadly characterized as a process for flushing material from an ionic liquid catalyst reactor by: passing a wash stream to a reaction zone to remove material from the reaction zone, the reaction zone configured to receive an ionic liquid catalyst and perform a reaction; passing the wash stream from a reaction zone to a solids separation zone; and, removing solid contaminant particles from the wash stream in the solids separation zone.

In at least one embodiment, the process includes passing a solvent to the solids separation zone to recover ionic liquid. It is contemplated that the solids separation zone comprises at least one vessel with a filter material. It is further contemplated that the process includes recovering the solvent.

Additional aspects, embodiments, and details of the invention are set forth in the following detailed description of the invention.

DETAILED DESCRIPTION OF THE DRAWINGS

In the drawings of the present invention, one or more embodiments are shown in which like numerals denote like elements and in which.

DETAILED DESCRIPTION OF THE INVENTION

One or more processes have been invented in which ionic liquid catalyst droplets are separated from a hydrocarbon phase by retaining the ionic liquid catalyst droplets on a retaining material for retaining ionic liquid catalyst droplets. Such retaining material may comprise an adsorbent material or a filter material. It is contemplated that the retained ionic liquid catalyst droplets are removed with a second fluid, i.e., a desorbent or a solvent; however, in some embodiments of the present invention, it is not necessary to do so. Furthermore, some of the ionic liquid catalyst may be recovered from a wash stream from a reactor. By removing the ionic liquid catalyst droplets from the hydrocarbon phase, the recovery of ionic liquid catalyst may be increased and the downstream equipment may be protected.

With these basic principles of the present invention in mind, one or more processes according to various aspects and embodiments of the present invention will now be described with the understanding that these processes are intended to be exemplary in nature and not limiting of the present invention.

Figure 1:
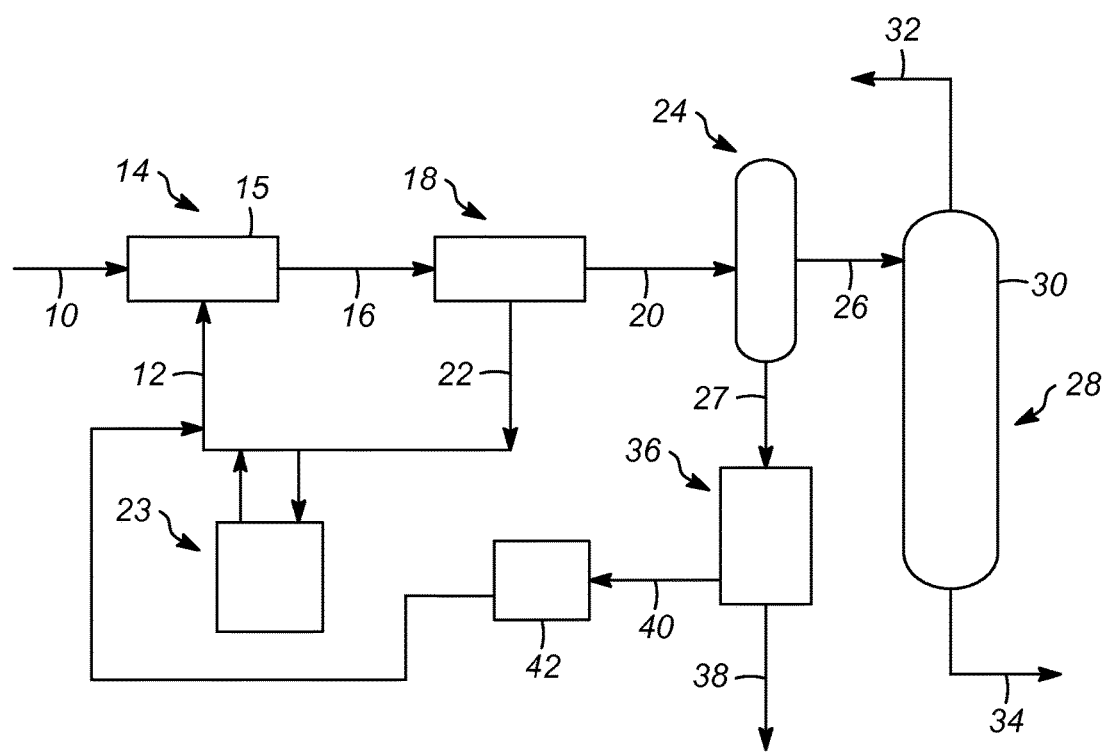
FIG. 1 shows a process flow diagram for one or more processes according to one or more embodiments of the present invention.

With reference to FIG. 1, a hydrocarbon conversion process utilizing at least one feature or embodiment of the present invention is illustrated in which a hydrocarbon feed 10 and an ionic liquid catalyst 12 comprising at least one ionic liquid are introduced into a reaction zone 14 having at least one reaction vessel 15.

The ionic liquid comprises an organic cation and an anion. Suitable cations include, but are not limited to, nitrogen-containing cations and phosphorus-containing cations. The ionic liquid can comprise phosphonium based ionic liquids, pyridinium based ionic liquids, imidazolium based ionic liquids, ammonium based ionic liquids, pyrrolidinium based ionic liquids, and lactamium based ionic liquids. Ammonium based ionic liquids include trialkyl and tetra alkyl ammonium based ionic liquids.

In some embodiments, the anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from $0<Al<0.25$ in the anion. Suitable anions include, but are not limited to, $AlCl_4^-$, $Al_2Cl_7^-$, $AlCl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$. In other embodiments, other anions could be used.

Various hydrocarbon conversion processes can occur in the reaction zone 14, including, but not limited to, alkylation, isomerization, oligomerization, and disproportionation. These reactions typically employ high shear mixing apparatus to provide intimate contact between the hydrocarbon feed 10 and the ionic liquid catalyst 12. For example, an alkylation reaction may be performed in the reaction zone, with olefins reacting with iso-paraffins, such as iso-butane, to provide an alkylate rich effluent stream with a high octane number that may be used for gasoline. Alkylate is the product of alkylation reactions and which comprises mostly iso-paraffins with five or more carbon atoms and, depending on the feed to the reactor, may also include some hydrocarbons with three or four carbon atoms. In such processes, the volume fraction of ionic liquid in the reaction zone is typically between 0.01 and 0.2, and the overall ratio of paraffins to olefins in the feed 10 is typically between 5 and 15 by mass. As will be appreciated, while it is depicted that a single hydrocarbon feed 10 is passed into the reaction zone, the olefins and paraffins in the hydrocarbon feed 10 may be separately added to the reaction zone 14 in one or more locations. Again, this is merely an exemplary reaction and other reactions, reactants, and products may be used in accordance with the present invention.

An effluent stream 16 from the reaction zone 14 comprises hydrocarbon conversion products, the ionic liquid catalyst, and may contain solvent, unconverted reactants, catalyst promoter such as hydrochloric acid, organic chlorides, or other compounds. The mass partition coefficient (concentration of soluble ionic liquid in the hydrocarbon phase divided by concentration in the ionic liquid phase at equilibrium) of ionic liquid in the effluent 16 is less than 10%, preferably less than 0.1% and more preferably less than 0.001%. The remainder of ionic liquid in the effluent 16 is contained in insoluble droplets. The effluent 16 is sent to a first separation zone 18 where the hydrocarbon conversion products separate from the ionic liquid catalyst forming a hydrocarbon phase 20 and an ionic liquid phase 22. This separation can be a phase separation as a result of the difference in the density of the immiscible phase 20 and the ionic liquid phase 22, although other methods could also be used, including for example, a coalescer material. The ionic liquid phase 22 can be recycled to the reaction zone 14, if desired, and, at least some of the ionic liquid phase 22 may be passed to a regeneration zone 23 to remove conjunct polymer from the ionic liquid catalyst.

Some small ionic liquid droplets remain in the hydrocarbon phase 20. This is typically a result of the high shear mixing used within the reaction zone to ensure good contact between the ionic liquid catalyst and the reactant hydrocarbons. As mentioned above, in some instances the presence of the ionic liquid catalyst in the hydrocarbon phase 20 can damage downstream processing equipment. Additionally, ionic liquid catalyst is relatively expensive and it is oftentimes desirable to recover and recycle as much ionic liquid catalyst as possible. Therefore, in various embodiments of the present invention, the hydrocarbon phase 20 containing the entrained droplets of ionic liquid is passed to a second separation zone 24.

In the second separation zone 24, the ionic liquid droplets are removed from the hydrocarbon phase 20 by a retaining material for retaining ionic liquid catalyst droplets. The second separation zone 24 will provide an ionic liquid catalyst lean hydrocarbon stream 26 that will comprise unreacted reactants from the reaction zone 14 and products from the hydrocarbon conversion reaction and an ionic liquid rich stream 27 which may comprise ionic liquid catalyst as well as solvent or desorbent. Accordingly, the ionic liquid catalyst lean hydrocarbon stream 26 may be passed to a fractionation zone 28 having a column 30 to separate the hydrocarbon conversion products and unreacted reactants, allowing an unreacted reactant stream 32 to be recycled to the reaction zone 14 and a product stream 34 to be passed to downstream processing. The further processing of the reactant stream 32 and the product stream 34 is not necessary for an understanding and practicing of the present invention.

In an alkylation reaction, the product stream 34 would comprise an alkylate product and the unreacted reactant stream 32 may comprise an iso-paraffin stream, such as iso-butane. Additionally, the ionic liquid catalyst lean hydrocarbon stream 26 will comprise at least approximately 10 wt %, or in some embodiments at least approximately 15 wt %, of $C_3$ hydrocarbons and $C_5$ to $C_9$ hydrocarbons (iso-paraffins) and at least 50 wt % of $C_4$ hydrocarbons (both normal paraffins and iso-paraffins). Additionally, depending on the temperature of the reaction, which is preferably between −10° and 60° C., and more preferably between 15° and 45° C., the ionic liquid catalyst lean hydrocarbon stream 26 will have a viscosity between 0.1 centipoise and 1 centipoise, and preferably between 0.1 centipoise and 0.3 centipoise.

Within the second separation zone 24, the retaining material for retaining ionic liquid catalyst droplets may comprise an adsorbent material, although other materials may be used. Oxides and oxide materials such as silica, silica gel, glass, glass beads, sand, and alumina could be used as adsorbents in granular, fiber, pellet, or other form. Salts such as $MgSO_4$ and $CaSO_4$ that are traditionally used as drying agents could be used as adsorbent material. Other salts could adsorb ionic liquid as well due to charge-dipole and dipole-dipole interactions. Ion exchange resins such as sulfonic acid resins would also be a possible adsorbent, as could fiber materials such as heteroatom containing polymers like Nylon-6 and other fibers such as wool. It is also believed that activated carbon and clays could be utilized as adsorbents. The second separation zone 24 may comprise multiple vessels with beds in a swing bed configuration or parallel beds which are periodically swung to desorption mode. Alternatively, the second separation zone 24 may comprise a single vessel operated in alternating modes of adsorption and desorption. By adsorption mode it is meant that the vessel or bed is retaining ionic liquid droplets from the hydrocarbon stream. By desorption mode, it is meant that the vessel or bed is receiving a desorbent or solvent and ionic liquid is being desorbed from the adsorbent material. The beds may be fluidized or fixed beds. In embodiments in which more than one vessel is used, it is contemplated that the vessels are operated independently of each other in adsorption mode and desorption mode.

In some instances it is desired merely to retain the ionic liquid catalyst droplets so as to minimize the amount of ionic liquid catalyst droplets that are passed to downstream equipment to avoid fouling or damaging the equipment. The ionic liquid catalyst may be burned off of the spent or saturated adsorbent under calcination conditions which would regenerate spent adsorbent allowing the adsorbent to be reused. Alternatively, the spent or saturated adsorbent may be disposed of as a waste product and replaced with a fresh adsorbent.

In some instances it may be desirable to recover some or all of the ionic liquid catalyst from the retaining material. Accordingly, a solvent or a desorbent may be used to remove the ionic liquid catalyst from the retaining material. For example, an ionic liquid precursor, a second and different ionic liquid, inert liquid, benzene, toluene, and quinoline may be used as a solvent. The desorbent could be something in which the ionic liquid is soluble and operate via a solubility mechanism, such as a chlorosilane or an organic halide such as methylene chloride, or chlorobenzene. In cases in which an ionic liquid with a halometallate ionic liquid is used, such a desorbent may either fully recover the ionic liquid (after being separated from the desorbent by separation), or recover the halide (i.e. chloride) form of the ionic liquid which could be converted to the active form by reactivation. Alternatively the desorbent could be a solvent which also hydrolyzes or coordinates the chloroaluminate anion of the ionic liquid catalyst, such as water, an alcohol, acetone, or acetonitrile. For example, aluminum oxides from the ionic liquid catalyst may be retained on the adsorbent and the cation of the ionic liquid catalyst may be highly soluble in the solvent and could be recovered from the eluent after desorption and either discarded or converted to the chloroaluminate form of the ionic liquid catalyst by removing the desorbent and adding aluminum chloride. One specific recovery method that is contemplated involves an alkylchloride, such as 2-chlorobutane or an alkyl chloride in iso-butane, being used as the desorbent. During desorption, ionic liquid catalyst would be dissolved in the alkylchloride. The ionic liquid, alkylchloride, iso-butane and any reaction products such as olefin and hydrochloric acid generated from the alkylchloride would be recycled to the reactor in the reaction zone.

In embodiments where the ionic liquid catalyst is being recovered from the retaining material, it is preferred that the adsorbent and desorbent are void of water in order to prevent oxidation or hydrolysis of the anion.

In embodiments which include an ion exchange resin, the ionic liquid catalyst cation could be recovered using an ion exchange desorbent such as an acid, for example hydrochloric acid, or ammonium or metal salt, preferably with chloride as the anion. The ion exchange desorbent would exchange for the ionic liquid catalyst cation which could then be recovered as a salt with the ion exchange anion (preferably chloride). The recovered ionic liquid could then be reactivated, for instance by addition of aluminum chloride.

Returning to FIG. 1, the ionic liquid rich stream 27 may be passed to a recovery zone 36 to separate the ionic liquid catalyst from the solvent or desorbent and provide a solvent or desorbent stream 38 and a desorbed ionic liquid catalyst stream 40. The desorbed ionic liquid catalyst stream 40 may be passed to the regeneration zone 23, or it may be passed to a reactivation zone 42 to reactivate the recovered ionic liquid catalyst and then passed to the reaction zone 15. The desorbent stream 38 can be recycled in the process. Again, while the recovery of the ionic liquid catalyst is possible, it is not necessarily required for practicing of the present invention. It is further contemplated, although not depicted as such, that the regeneration zone 23 is disposed after the reaction zone 15 and before the second separation 24, so that at least a portion of the ionic liquid undergoes regeneration before being separated and removed from the hydrocarbon phase by the retaining material. Additionally, alternatively, or both, it is contemplated that the regeneration zone 23 includes one or more separation zones to separate a mixture of hydrocarbons and ionic liquid catalyst into separate phases, and remove ionic liquid catalyst droplets from the hydrocarbons phase. Such separation zones may be similar to separation zones 18 and 24. This may be desirable if, for example, the regeneration process utilizes a hydrocarbon phase.

Figure 2:
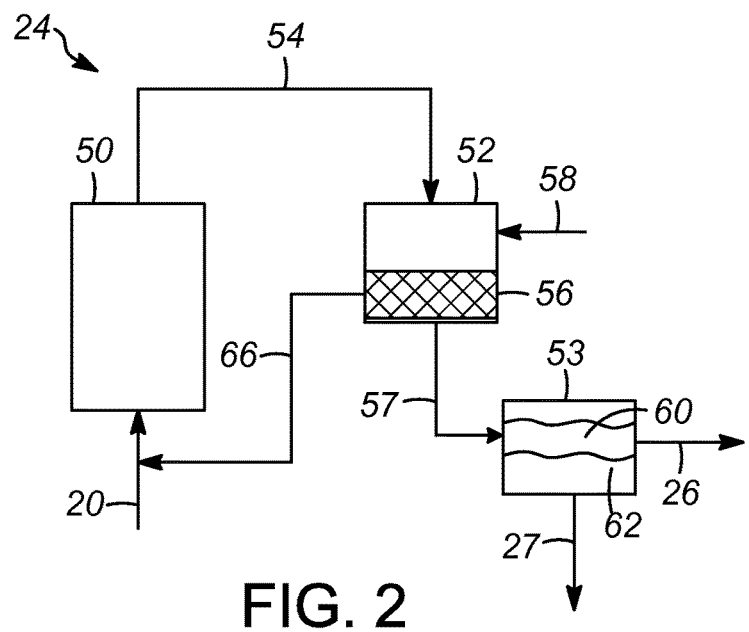
FIG. 2 shows a process flow diagram for a separation zone according to one or more embodiments of the present invention.

Turning to FIG. 2, an exemplary configuration for the second separation 24 is shown in which three vessels 50, 52, 53 are shown, but it should be appreciated that more or less than three vessels may be used. The hydrocarbon phase 20 containing the entrained droplets of ionic liquid is passed to the first vessel 50, which includes retaining material for retaining ionic liquid. The ionic liquid droplets will be retained on the retaining material and a mixture 54 of the hydrocarbon phase 20 and the material for retaining ionic liquid are passed to the second vessel 52. The second vessel 52 includes a filter material 56 or other structure or material which physically prevents the solids from permeating, allowing the retaining material to be collected. A solvent or desorbent 58 is passed into the second vessel 52 and will remove the ionic liquid catalyst from the retaining material. A stream 57 comprising a mixture of hydrocarbons and ionic liquid catalyst can be passed to the third vessel 53 in which a hydrocarbon phase 60 and an ionic liquid phase 62 will separate by gravity. The ionic liquid rich stream 27 can be recycled to the reactor, or it may be reactivated, for example with $AlCl_3$, after separation from the solvent or desorbent. The ionic liquid catalyst lean hydrocarbon stream 26 can be processed as discussed above with respect to FIG. 1.

It is contemplated that the retaining material is recycled back from the second vessel 52 in a recycle stream 66, and, for example, mixed with the hydrocarbon phase 20. Alternatively, the retaining material may merely accumulate within the second vessel for a certain amount of time, after which the material would be removed.

Figure 3:
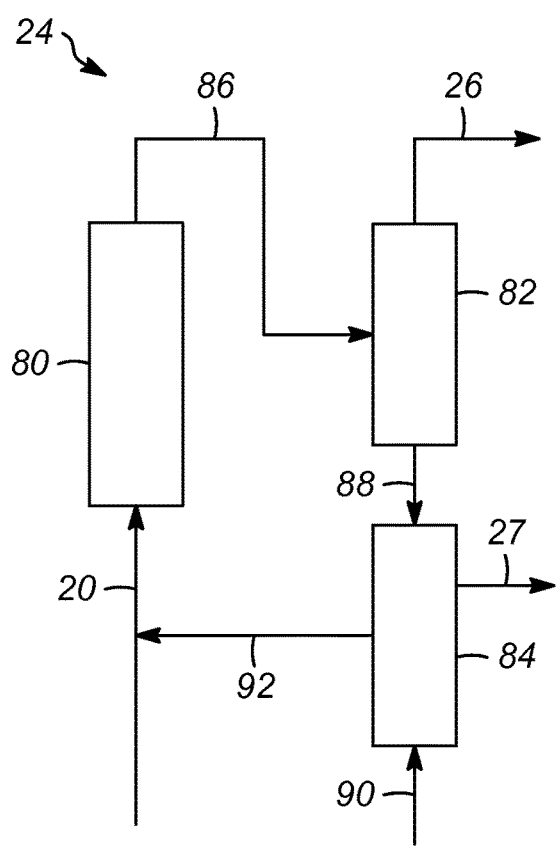
FIG. 3 shows another process flow diagram for a separation zone according to one or more embodiments of the present invention; and, FIG. 4 shows another process flow diagram for a process according to one or more embodiments of the present invention.

As shown in FIG. 3, another exemplary configuration is shown in which the second separation zone 24 comprises three vessels 80, 82, 84. The first vessel 80 receives the hydrocarbon phase 20 containing the entrained droplets of ionic liquid. The first vessel 80 contains the retaining material. The ionic liquid droplets will be retained on the retaining material and a mixture 86 of the hydrocarbon phase 20 and the retaining material are passed to the second vessel 82.

In the second vessel 82, a hydrocarbon phase will separate from the mixture and the ionic liquid catalyst lean hydrocarbon stream 26 can be removed and processed as discussed above. An optional hydrocarbon lean stream 88, which includes the retaining material, may be passed to the third vessel 84 (which may be a separate zone in the second vessel 82) that will also receive a desorbent or solvent stream 90 with a counter current flow. The ionic liquid rich stream 27 including desorbent/solvent may be passed to a separation zone to separate the ionic liquid from the desorbent as discussed above. A recycle stream 92 of retaining material may be passed back to the first vessel, for example by combining with the hydrocarbon phase 20.

In some cases, the recovered ionic liquid may not be in active form when recovered, therefore, it is contemplated that the recovered ionic liquid is reactivated with a reactivation agent, for example $AlCl_3$.

Figure 4:
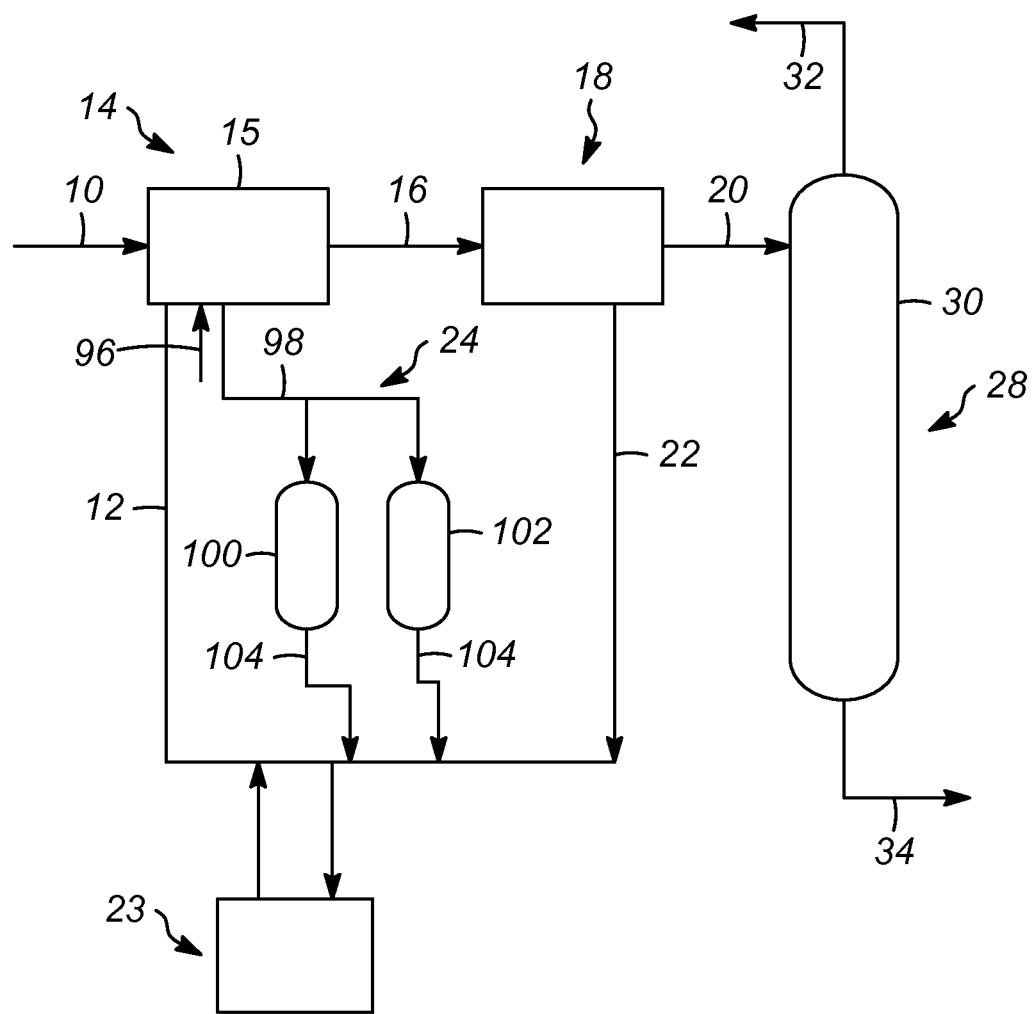

Turning to FIG. 4, another embodiment of the present invention is shown in which the solvent/desorbent is used as a wash fluid to remove solids, films, deposits, gels, sludge, conjunct polymer, salts formed by ionic liquid catalyst or any other similar material (collectively herein "contaminant solids") from the reactor, separator, or other process vessels. While it is contemplated that the configurations of the above discussed embodiments may be used in this embodiment of the present invention, it is also contemplated that the second separation zone 24 is operated independently of the first separation zone 18. For example, in a wash or flush mode, a reactor, such as reactor 15, can be isolated from other reactors and equipment, and a wash stream 96 comprising solvent or desorbent can be introduced to the unit, and passed, via valves (not shown) into the reactor 15 to flush out contaminant solids. A mixture 98 of the solids and wash fluid can be passed to a separation vessel 100 in the second separation zone 24 having a retaining material. The contaminant solids will accumulate on the retaining material until the retaining material needs to be replaced. At that time, the second vessel 102 can be used to accumulate the solids on the retaining material. From either vessel 100, 102, a contaminant solids free liquid stream 104 can be passed to reactor 15. If the liquid stream 104 comprises solvent/desorbent and ionic liquid catalyst, it can be separated and reactivated as discussed above. The vessels 100, 102 can be operated in a lead-lag configuration or in a parallel configuration. By removing any contaminant solids from the reactor, the reactor can be more effectively operated. This operation can be conducted continuously or periodically whenever contaminant solids, such as films, deposits, gels, sludge, and conjunct polymer accumulate in a vessel. Additionally, it is further contemplated that the wash stream 96 passes from the reactor 15 to the first separation zone 18 (via a line typically carrying effluent 16) and also remove solid contaminants from the first separation zone 18. Valves (not shown) would control the flow of the mixed stream (for example via a line typically carrying ionic liquid phase 22 from the first separation zone) to one of the vessels 102, 104 discussed above. It is contemplated that in some embodiments the solvent/desorbent will dissolve the solid ionic liquid and allow the now dissolved ion of the ionic liquid salt to be recovered.

In many of the embodiments of the present invention, the ionic liquid catalyst droplets have been removed from the hydrocarbon phase to allow for recovery, if desired, and to protect downstream equipment.

Additionally, by providing processes for cleaning and retaining contaminant solids, the reactors used in ionic liquid catalyst processes can be maintained.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for removing ionic liquid catalyst from an effluent stream including hydrocarbons and an ionic liquid catalyst, wherein the effluent stream is provided by an ionic liquid catalyst reaction zone, the process comprising:
    a first stage separation step comprising separating a mixture comprising hydrocarbons and ionic liquid catalyst into a hydrocarbon phase and an ionic liquid catalyst phase, the hydrocarbon phase including ionic liquid catalyst droplets;
    a second stage separation step comprising separating the ionic liquid catalyst droplets from the hydrocarbon phase by retaining the ionic liquid catalyst droplets with a retaining material for retaining ionic liquid catalyst droplets in a first vessel;
    passing a stream comprising the hydrocarbon phase and the retaining material with retained ionic liquid catalyst droplets to a second vessel;
    collecting the retaining material with retained ionic liquid catalyst in the second vessel to provide an ionic liquid catalyst lean hydrocarbon stream from the second vessel, the ionic liquid catalyst lean hydrocarbon stream having a viscosity less than 1 centipoise; and,
    removing the retained ionic liquid catalyst from the retaining material in the second vessel with at least one of a solvent and a desorbent,
    wherein the hydrocarbon phase from the first stage separation step is passed directly to the second stage separation step, and at least a portion of the recovered ionic liquid catalyst is returned to the ionic liquid catalyst reaction zone;
    wherein the retaining material comprises an adsorbent material selected from the group consisting of alumina, silica, silica gel, glass, sand, a salt, an ion exchange resin, activated carbon, a polymer, a natural fiber, a zeolite, a molecular sieve, and a combination thereof; and
    wherein the second vessel includes a filter material to collect the retaining material with retained ionic liquid catalyst in the second vessel.

2. The process of claim 1 further comprising:
desorbing ionic liquid catalyst from the adsorbent material with a desorbent.

3. The process of claim 2 further comprising:
regenerating the adsorbent material after the ionic liquid catalyst has been desorbed from the adsorbent material.

4. The process of claim 1 further comprising:
reactivating at least a portion of the ionic liquid catalyst that has been recovered from the retaining material.

5. The process of claim 4 wherein aluminum chloride is used to reactivate the ionic liquid catalyst.

* * * * *